(12) United States Patent  
Matsuda et al.

(10) Patent No.: US 7,901,393 B2  
(45) Date of Patent: Mar. 8, 2011

(54) DISPOSABLE PULL-ON GARMENT

(75) Inventors: Toshiyuki Matsuda, Akashi (JP); Kenji Fujimoto, Kobe (JP); Hiroshi Nakahata, Kobe (JP); Eiro Fukuda, Mason, OH (US); Masaharu Nishikawa, Cincinnati, OH (US); Stephan David Conrad, Batavia, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 77 days.

(21) Appl. No.: 11/197,203

(22) Filed: Aug. 4, 2005

(65) Prior Publication Data

US 2006/0030831 A1 Feb. 9, 2006

Related U.S. Application Data

(60) Provisional application No. 60/599,206, filed on Aug. 5, 2004.

(51) Int. Cl.  
*A61F 13/15* (2006.01)  
*A61F 13/20* (2006.01)

(52) U.S. Cl. .................................. 604/392; 604/386

(58) Field of Classification Search .......... 604/393–402, 604/386, 392  
See application file for complete search history.

(56) References Cited

U.S. PATENT DOCUMENTS

| 4,704,115 | A | * | 11/1987 | Buell ....................... 604/385.26 |
| 5,685,874 | A | * | 11/1997 | Buell et al. ................... 604/396 |
| 5,769,838 | A | | 6/1998 | Buell et al. |
| 5,931,827 | A | | 8/1999 | Buell et al. |
| 7,060,058 | B2 | * | 6/2006 | Otsubo et al. ............ 604/385.27 |

FOREIGN PATENT DOCUMENTS

| EP | 873738 A2 | 10/1998 |
| EP | 1 184 012 A1 | 3/2002 |
| JP | H4 144558 | 5/1992 |
| WO | WO 96/31178 | 10/1996 |
| WO | WO 0101904 A1 * | 1/2001 |
| WO | WO0101904 A1 | 1/2001 |
| WO | WO2004105664 A1 | 12/2004 |
| WO | WO2004105665 A1 | 12/2004 |

OTHER PUBLICATIONS

PCT International Search Report mailed Dec. 5, 2005—7 Pages.

* cited by examiner

*Primary Examiner* — Melanie J Hand  
(74) *Attorney, Agent, or Firm* — Charles R. Ware; John G. Powell

(57) ABSTRACT

A disposable pull-on garment is disclosed, The pull-on garment comprises a ring-like elastic belt. The ring-like elastic belt comprises a front belt portion and a back belt portion comprising a belt layer and a belt elastic material joined to the belt layer. Each ring-like elastic belt portion has a central panel, and left and right side panels contiguous with its central panel. The central panel of the front belt portion is joined to the front waist panel of the absorbent main body. The central panel of the back belt portion is joined to the back waist panel of the absorbent main body. The respective left and right side panels of the front belt portion and the back belt portion are joined together at or adjacent to the respective left and right side edges to form the waist opening and the two leg openings. The longitudinal lengths of the side panels of the back belt portion are greater than the longitudinal lengths of the respective side panels of the front belt portion.

6 Claims, 13 Drawing Sheets

DISPOSABLE PULL-ON GARMENT

CROSS REFERENCE TO RELATED APPLICATION

This Application claims the benefit of U.S. Provisional Application No. 60/599,206, filed Aug. 5, 2004.

FIELD OF THE INVENTION

The present invention relates to disposable pull-on garments which are donned by inserting the wearer's legs into the leg openings and sliding the garment up into position about the lower torso.

BACKGROUND OF THE INVENTION

Many pull-on diapers use elastic elements secured in an elastically contractible condition in the waist and leg openings. Typically, in order to insure full elastic fit about the leg and the waist such as is provided with durable undergarments, the leg openings and waist opening are encircled with elasticized bands of rubber or other materials positioned along the curve of the opening. Examples of such pull-on diapers are disclosed in EP 1 184 012 A1 published on Mar. 6, 2002. The pull-on diaper disclosed therein comprises an absorbent body and an exterior member covering the absorbent body and forming a contour of the diaper. The absorbent body is substantially rectangular and comprises a liquid-permeable topsheet, a liquid-impermeable backsheet and an absorbent core interposed therebetween. The leg and waist elastic members are installed into the exterior member to form an elasticized leg opening and an elasticized waist opening. The longitudinal sides of the exterior member are trimmed to form a leg opening. While trimming the longitudinal side of the exterior member allows to form a desired shape of curved leg opening, it requires an additional process for trimming and wastes raw materials.

Another example of pull-on diapers is disclosed in Japanese Laid-open Publication No. H4-144558 published on May 19, 1992. The pull-on diaper disclosed therein comprises an absorbent main body and an elastic belt joined to the front region and the back region of the absorbent main body. The elastic belt extends in the transverse direction of the diaper and the absorbent main body extends in the longitudinal direction. The upper end of the elastic belt defines a waist opening. The lower end of the elastic belt and the longitudinal side of the absorbent main body jointly define a leg opening. The elastic belt disclosed therein comprises a front belt and a back belt which have the same longitudinal length between the upper end and the lower end. While such a front belt configuration allows the diaper to fit the wearer's body between the front thigh and the abdomen, the back belt having the same longitudinal length between the upper end and the lower end as the front belt does not cover the wearer's buttock to the extent that the diaper appearance looks like a real garment.

Based on the foregoing, there is a need for a disposable pull-on garment effectively covering the wearer's buttock at the back while allowing a snug fitment at the front.

SUMMARY OF THE INVENTION

The present invention is directed to a disposable pull-on garment having a waist opening and two leg openings and extending in a longitudinal direction and a transverse direction. The pull-on garment comprises an absorbent main body and a ring-like elastic belt. The absorbent main body comprises a liquid pervious topsheet, a liquid impervious backsheet, and an absorbent core disposed therebetween. The absorbent main body has left and right longitudinally extending side edges, front and back transversely extending end edges, longitudinally opposing front and back waist panels, and a crotch panel between the waist panels. The ring-like elastic belt comprises a front belt portion and a back belt portion. Each of the ring-like belt comprises a belt layer and a belt elastic material joined to the belt layer. Each of the ring-like elastic belt has transversely extending proximal and distal edges, longitudinally extending left and right side edges connecting the proximal and distal edges, the proximal edge being located closer than the distal edge relative to the crotch panel of the absorbent main body, a central panel, and left and right side panels contiguous with its central panel. Each side panel having a longitudinal length defined by the respective side edge of the respective belt portion. The central panel of the front belt portion is joined to the front waist panel of the absorbent main body. The central panel of the back belt portion is joined to the back waist panel of the absorbent main body. The respective left and right side panels of the front belt portion and the back belt portion are joined together at or adjacent to the respective left and right side edges to form the waist opening and the two leg openings. The longitudinal lengths of the side panels of the back belt portion are greater than the longitudinal lengths of the respective side panels of the front belt portion.

BRIEF DESCRIPTION OF THE DRAWINGS

While the specification concludes with claims particularly pointing out and distinctly claiming the subject matter which is regarded as forming the present invention, it is believed that the invention will be better understood from the following description which is taken in conjunction with the accompanying drawings and which like designations are used to designate substantially identical elements, and in which:

DETAILED DESCRIPTION OF THE INVENTION

As used herein, the term "pull-on garment" refers to articles of wear which have a defined waist opening and a pair of leg openings and which are pulled onto the body of the wearer by inserting the legs into the leg openings and pulling the article up over the waist. The term "disposable" is used herein to describe garments which are not intended to be laundered or otherwise restored or reused as a garment (i.e., they are intended to be discarded after a single use and, preferably, to be recycled, composted or otherwise disposed of in an environmentally compatible manner). The pull-on garment is also preferably "absorbent" to absorb and contain the various exudates discharged from the body. A preferred embodiment of the pull-on garment of the present invention is the disposable absorbent pull-on garment, pull-on diaper 20, shown in FIG. 1. As used herein, the term "pull-on diaper" refers to pull-on garments generally worn by infants and other incontinent individuals to absorb and contain urine and feces. It should be understood, however, that the present invention is also applicable to other pull-on garments such as training pants, incontinent briefs, feminine hygiene garments or panties, and the like.

Figure 1:
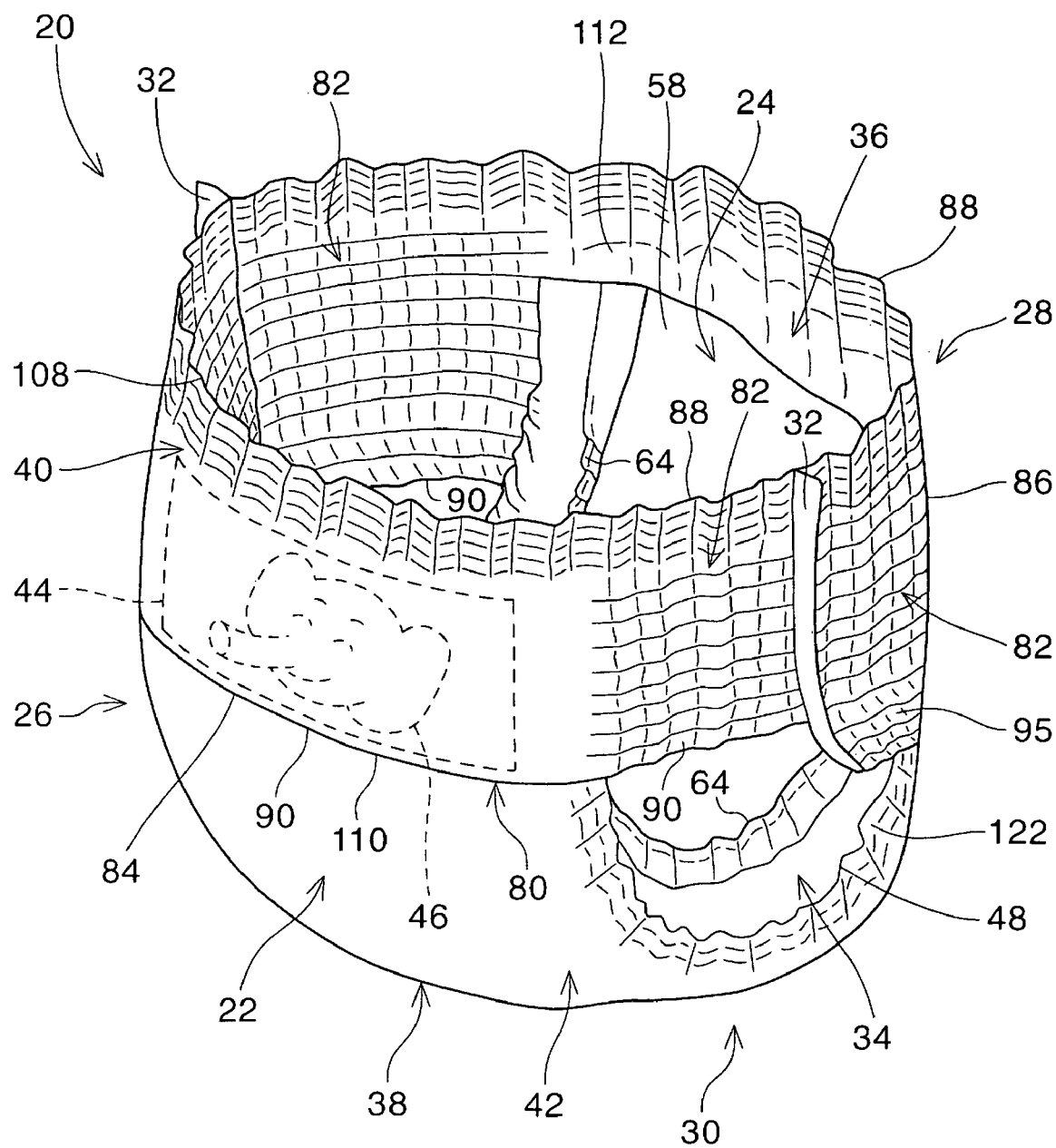
FIG. 1 is a perspective view of the disposable pull-on garment of the present invention in a typical in-use configuration.

FIG. 1 is a perspective view of the pull-on diaper 20 of the present invention. The pull-on diaper 20 has a longitudinal centerline L1 and a transverse centerline T1. The pull-on diaper 20 has an outer surface 22, an inner surface 24 opposed to the outer surface 22, a front region 26, a back region 28, a crotch region 30, and seams 32 which join the front region 26 and the back region 28 to form two leg openings 34 and a waist opening 36. The diaper 20 comprises an absorbent main body 38 (hereinafter may be referred to as "main body") to cover the crotch region of the wearer, a ring-like elastic belt 40 (hereinafter may be referred to as "elastic belt" or "belt") extending transversely about the waist opening 36, and an outer cover layer 42 to cover the main body 38. The elastic belt 40 defines the waist opening 36. The elastic belt 40 and the main body 38 and/or the outer cover layer 42 jointly define the leg opening 34. Alternatively, the elastic belt 40 and the outer cover layer 42 may jointly define the leg opening 34. The pull-on diaper 20 also has a patch sheet 44 printed with a graphic 46 thereon which may be disposed in the front region 26 and/or the back region 28.

The absorbent main body 38 absorbs and contains body exudates disposed on the main body 38. In the embodiment shown in FIG. 2, the main body 38 has a generally rectangular shape having a longitudinal centerline L2, a transverse centerline T2, left and right longitudinally extending side edges 48 (hereinafter may be referred to as "longitudinal side edge") and front and back transversely extending end edges 50 (hereinafter may be referred to as "transverse end edge"). The main body 38 also has a front waist panel 52 positioned in the front waist region 26 of the diaper 20, a back waist panel 54 positioned in the back waist region 28, and a crotch panel 56 between the front and back waist panels 52, 54 in the crotch region 30.

Figure 3:
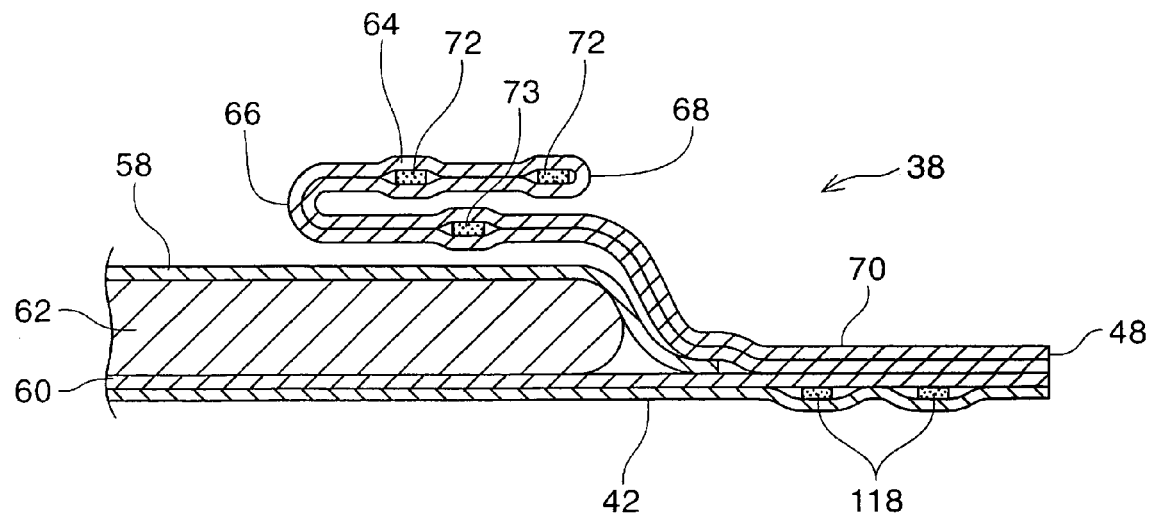
FIG. 3 is a cross-sectional view of FIG. 2 taken along the line III-III.
Figure 4:
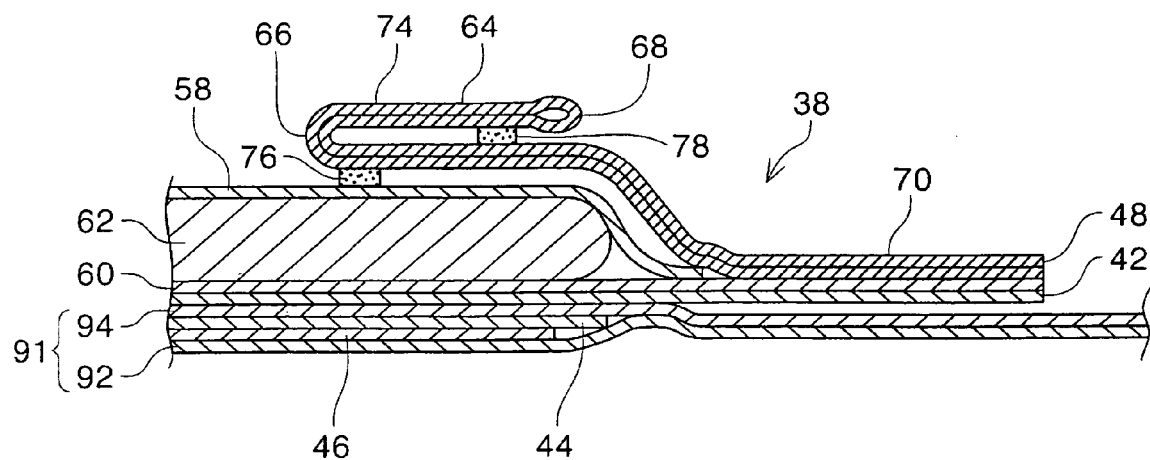
FIG. 4 is a cross-sectional view of FIG. 2 taken along the line IV-IV.
Figure 5:
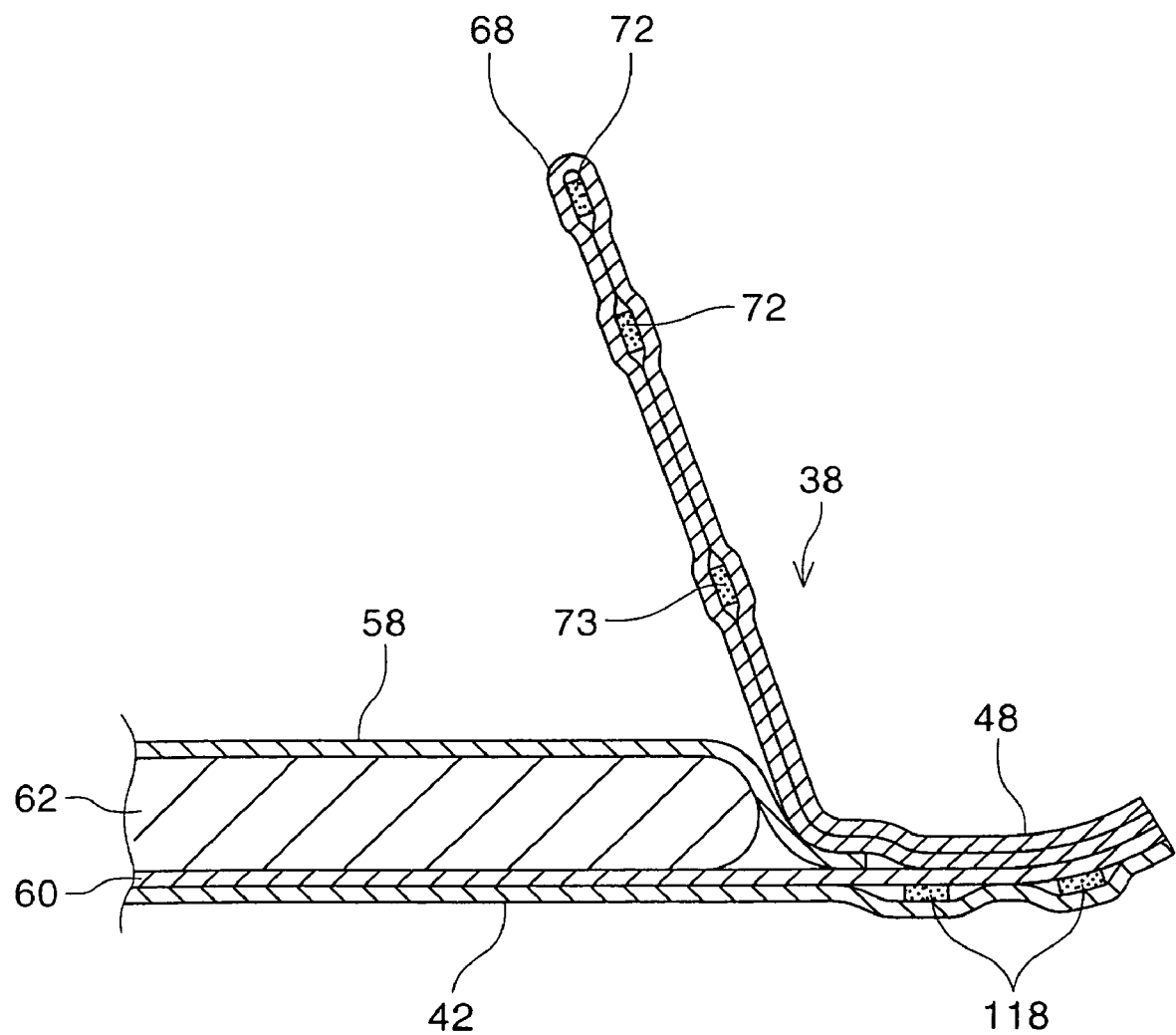
FIG. 5 is a cross-sectional view showing a typical in-use configuration of the portion shown in FIG. 3.

The main body 38 comprises a liquid pervious topsheet 58, a liquid impervious backsheet 60 and an absorbent core 62 disposed therebetween. The main body 38 may additionally comprise a barrier leg cuff 64 disposed along the longitudinal side edge 48. The barrier leg cuff 64 provides improved containment of liquids and other body exudates in the crotch region 30. The barrier leg cuff 64 shown in FIG. 3 comprises a single layer of material which is folded into two layers. The barrier leg cuff 64 extends from the longitudinal side edge 48 toward the longitudinal centerline L2 and then is folded along the folding line 66 back toward the longitudinal side edge 48. The barrier leg cuff 64 has two barrier cuff elastic materials 72 adjacent the distal portion 68 and one barrier cuff elastic material 73 adjacent the proximal portion 70 of the barrier leg cuff 64. The proximal portion 70 of the barrier leg cuff 64 is joined to the backsheet 60 adjacent the longitudinal side edge 48. The portion of the barrier leg cuff 64 along the folding line 66 and the distal portion 68 are free from attachment to any portion of the main body 38 in the crotch panel 56 such that the barrier leg cuff 64 stands up toward the wearer's body as shown in FIG. 5 when the diaper 20 is used. The transverse end 74 of the barrier leg cuff 64 is joined to the topsheet 58 adjacent the folding line 66 by an attachment means 76 which may be any known means such as an adhesive and is joined onto the barrier leg cuff 64 itself along the distal portion 68 by an attachment means 78 which may be any known means such as an adhesive as shown in FIG. 4.

The liquid pervious topsheet 58 is preferably positioned adjacent the body-facing surface of the absorbent core 62 and may be joined thereto and/or to the backsheet 60 by any attachment means known in the art. The liquid impervious backsheet 60 is generally that portion of the diaper 20 positioned adjacent the garment-facing surface of the absorbent core 62 and prevents the exudates absorbed and contained therein from soiling articles that may contact the diaper 20. The absorbent core is positioned between the topsheet 58 and the backsheet 60 and absorbs and retains liquids such as urine and other certain body exudates. The topsheet 58, the backsheet 60 and the absorbent core may be manufactured any known materials. Suitable topsheet materials may include porous foams; reticulated foams; apertured plastic films; or woven or nonwoven webs of natural fibers (e.g., wood or cotton fibers), synthetic fibers (e.g., polyester or polypropylene fibers), or a combination of natural and synthetic fibers. Suitable backsheet materials may include breathable materials that permit vapors to escape from the diaper while still preventing exudates from passing through the backsheet. Suitable absorbent core materials may include creped cellulose wadding; meltblown polymers, including coform; chemically stiffened, modified or cross-linked cellulosic fibers; tissue, including tissue wraps and tissue laminates; absorbent foams; absorbent sponges; superabsorbent polymers; absorbent gelling materials; or any other known absorbent material or combinations of materials.

The outer cover layer 42 is disposed on the outer surface 22 of the diaper 20 and covers the crotch panel 56 of the absorbent main body 38. The outer cover layer 42 may extend into and cover the front waist panel 52 and the back waist panel 54 of the main body 38. The outer cover layer 42 is directly joined to and covers the liquid impervious backsheet 60 of the main body 38. The central panel 80 of the front and back belt 84, 86 portion (explained herein below) is joined to the front waist panel 52 and the back waist panel 54 of the main body 38 through the outer cover layer 42. Thus, the outer cover layer 42 is sandwiched between the front and back belt portion 84, 86 and the liquid impervious backsheet 60 of the main body 38. In the embodiment shown in FIGS. 2 and 3, the outer cover layer 42 is coextensive with the liquid impervious backsheet 60. The leg elastic material 118 is disposed so as to extend generally longitudinally along the longitudinal side edge 48 of the main body 38. The leg elastic material 118 may be disposed at least in the crotch region 30 of the diaper 20 or may be disposed along the entirety of the longitudinal side edge 48.

The outer cover layer 42 comprises a material separate from the material of the inner layer 94 and the outer layer 92 constituting the elastic belt 40. The outer cover layer 42 may comprise two of more layer of materials. The outer cover layer 42 may comprise any known materials and may comprise materials as used for the front and back belt portion 84, 86 as explained above. Preferably the outer cover layer 42 comprises a single layer of nonwoven web of synthetic fibers. More preferably, the outer cover layer 42 comprises a single layer of hydrophobic, non-stretchable nonwoven material.

Figure 7:
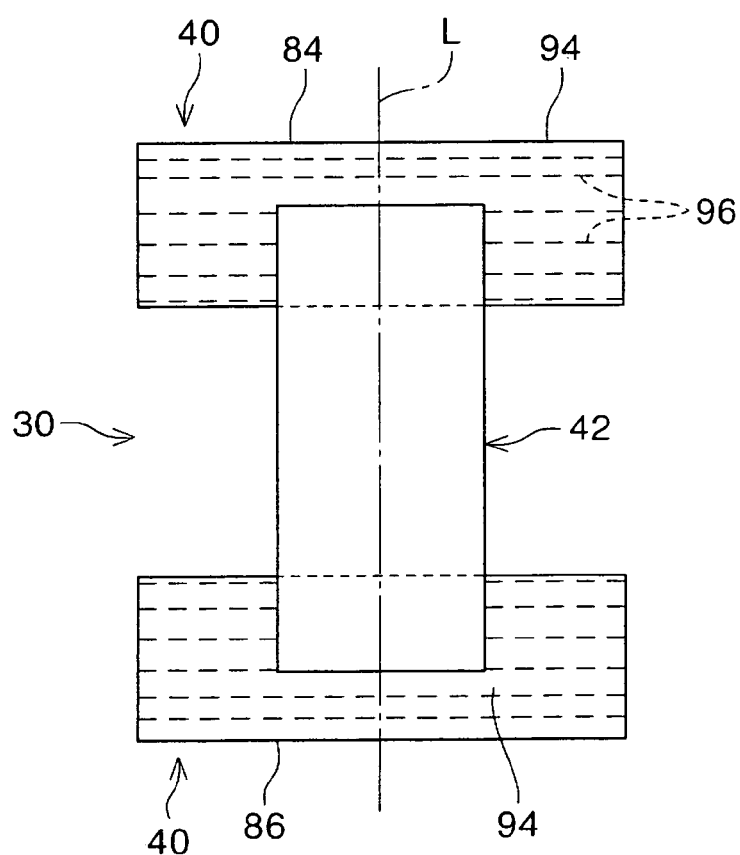
FIG. 7 is a schematic top plan view of the combination of the ring-like elastic belt and the outer cover layer in its flat uncontracted condition without showing an absorbent man body.
Figure 8:
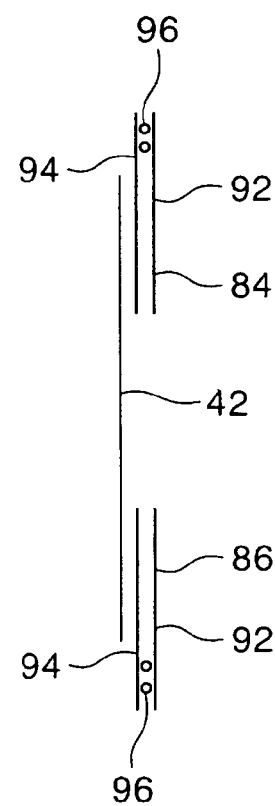
FIG. 8 is a schematic cross-sectional view of FIG. 7 taken along the longitudinal centerline L.

FIG. 7 shows a schematic top plan view of a combination of a ring-like elastic belt and an outer cover layer of the present invention without showing an absorbent main body. FIG. 8 is a schematic cross-sectional view of FIG. 7 taken along the longitudinal centerline L. The front and back belt portion 84, 86 of the ring-like elastic belt 40 comprises two layers of nonwoven to hold the belt elastic materials 96. However, the ring-like elastic belt 40 formed with two layers of nonwoven (inner layer 94 and outer layer 92) does not extend into the crotch region 30 of the diaper. Instead, the outer cover layer 42 comprising a single layer of nonwoven is disposed in the crotch region 30. This structure is less costly, allows the crotch region 30 of the diaper to be less bulky and eliminates various drawbacks of conventional pull-on diaper. The outer cover layer 42 comprising a nonwoven material also provides a cloth-like appearance together with the ring-like elastic belt 40 comprising a nonwoven material.

The ring-like elastic belt 40 extends transversely about the waist opening 36 of the diaper 20 and acts to dynamically create fitment forces and to distribute the forces dynamically generated during wear. The elastic belt 40 comprises a front belt portion 84 and a back belt portion 86 (hereinafter may be referred to as "front and back belt portion 84, 86). Each of the front belt portion 84 and the back belt portion 86 has a central panel 80F, 80B and side panels 82F, 82B contiguous with the central panel 80F, 80B and positioned transversely outward from the central panel 80F, 80B. Herein, a portion of a front member and a portion of a back member may be indicated by a reference number with "F" suffix and "B" suffix, respectively, as necessary. Therefore, the "central panel 80F, 80B" for example indicates the "front central panel 80F" and the "back central panel 80B". The "central panel 80" also may mean the "front central panel 80F" and the "back central panel 80B". Each of the front belt portion 84 and the back belt portion 86 has a transversely extending distal edge 88F, 88B, a transversely extending proximal edge 90F, 90B, and longitudinally extending left and right side edges 89F, 89B. Herein, the term "proximal" is used to indicate the position of a "proximal" portion being closer relative to the crotch panel of the main body than the position of a "distal" portion. Therefore, the proximal edge 90F, 90B is located closer than the distal edge 88F, 88B relative to the crotch panel 56 of the main body 38. The front and back belt portions 84, 86 are joined at or adjacent the side edges 89F, 89B at the seams 32 to form a pull-on diaper having a waist opening 36 and two leg openings 34. The front central panel 80F may partly or entirely overlap with the front waist panel 52 of the main body 38. The back central panel 80B may partly or entirely overlap with the back waist panel 54 of the main body 38. However, the central panel 80F, 80B does not extend into the crotch panel 56 of the main body 38 and is not disposed in the crotch panel 56. In the embodiment shown in FIG. 2, the central panel 80F, 80B partly overlaps with and is joined to the front waist panel 52 and the back waist panel 54, respectively.

Figure 2:
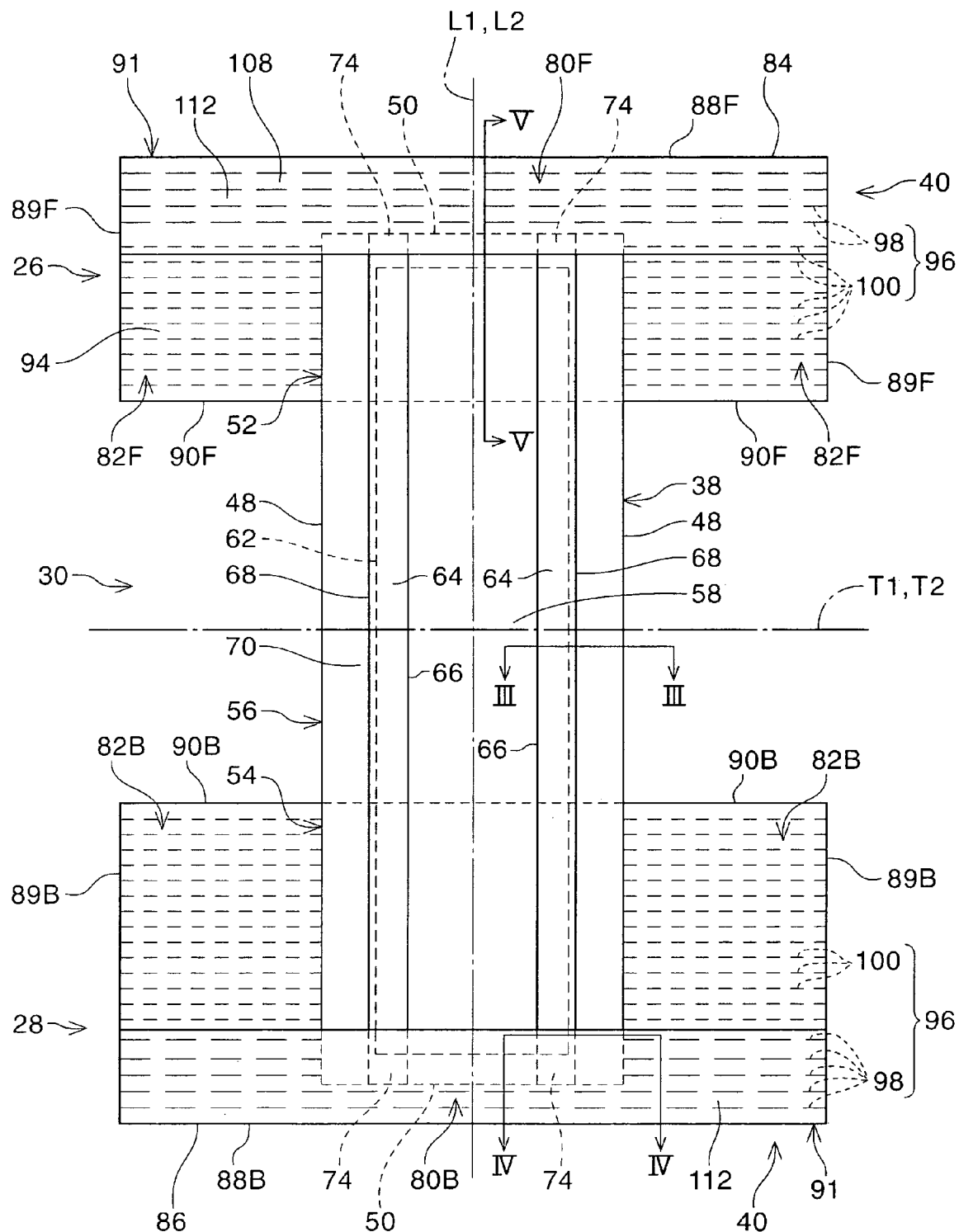
FIG. 2 is a top plan view of the pull-on garment in its flat uncontracted condition showing the inner surface.
Figure 6:
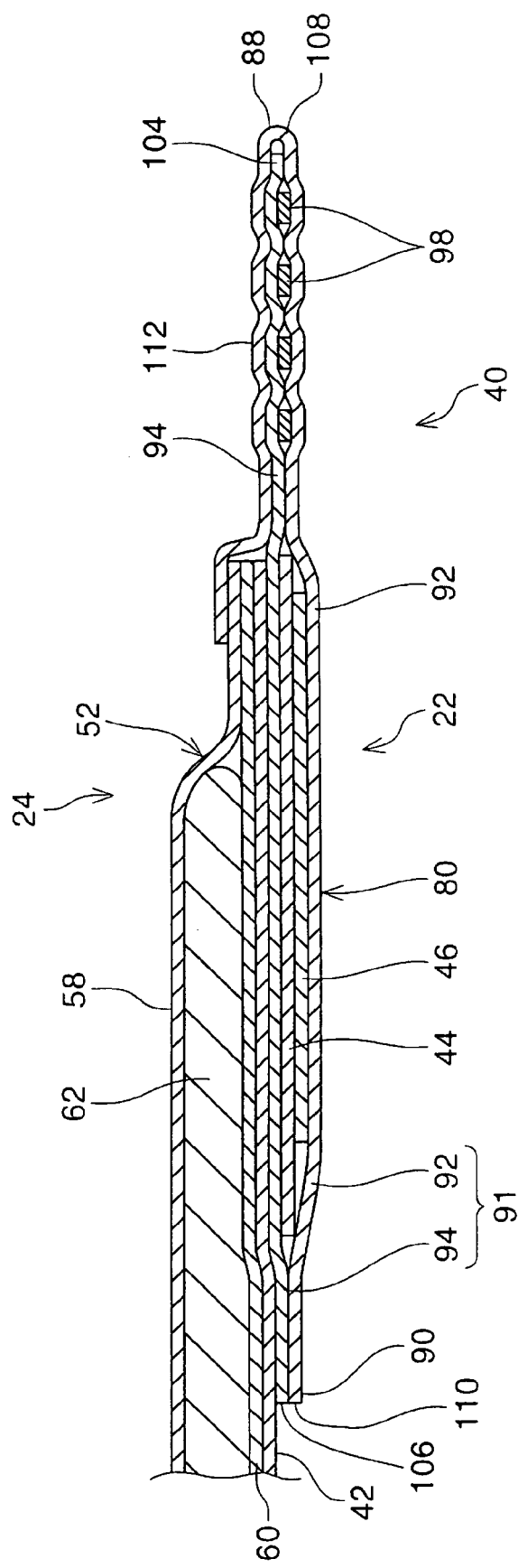
FIG. 6 is a cross-sectional view of FIG. 2 taken along the line V-V.

The ring-like elastic belt 40 comprises a belt layer 91 including an outer layer 92. The belt layer 91 may further comprise an inner layer 94. A belt elastic material 96 is interposed between the outer layer 92 and the inner layer 94. The front belt portion 84 and the back belt portion 86 may comprise the same materials and/or may have the same structure. Alternatively, the front belt portion 84 and the back belt portion 86 may comprise different materials and/or may have different structures. In the embodiment of FIG. 2, the front belt portion 84 and the back belt portion 86 generally have the same layer structure. Referring to FIG. 6, the inner layer 94 has a transversely extending distal end 104 and a transversely extending proximal end 106. The outer layer 92 has a transversely extending distal end edge 108 and a transversely extending proximal end edge 110. The inner layer 94 is almost coextensive with the contour of the front and back belt portion 84, 86. Alternatively, the inner layer 94 may be smaller than the size of the front and back belt portion 84, 86. The outer layer 92 of the belt layer 91 is longer than the size of the inner layer 94 in the longitudinal direction and an end flap 112 of the outer layer 92 is folded to cover the distal end 104 of the inner layer 94 at the waist opening 36 and to form a distal end edge 108 of the outer layer 92. The inner layer 94 of the belt layer 91 may also have an end flap which may be folded together with the end flap 112 of the outer layer 92. The end flap of the inner layer 94 may be longer or shorter than or equal to the end flap of the outer layer 92. Alternatively, the end flap 112 may be eliminated such that the outer layer 92 terminates at the waist opening 36 to form the distal end edge 108. In the embodiment shown in FIGS. 2 and 6, the distal end edge 108 and the proximal end edge 110 of the outer layer 92 correspond to the distal edge 88 and the proximal edge 90 of the front and back belt portion 84, 86, respectively. The outer layer 92 surrounded by the distal end edge 108 and the proximal end edge 110 defines the shape of the front and back belt portion 84, 86 in the embodiment shown in FIGS. 2 and 6.

The front and back belt portion 84, 86 may comprise any known materials. Suitable material for the front and back belt portion 84, 86 can be manufactured from a wide range of materials such as plastic films; apertured plastic films; woven or nonwoven webs of natural materials (e.g., wood or cotton fibers), synthetic fibers (e.g., polyolefins, polyamides, polyester, polyethylene, or polypropylene fibers), or a combination of natural and/or synthetic fibers; or coated woven or nonwoven webs. Preferably the belt comprises a nonwoven web of synthetic fibers. The belt portion may comprise a stretchable nonwoven. More preferably, the belt portion comprises an inner hydrophobic, non-stretchable nonwoven material and an outer hydrophobic, non-stretchable nonwoven material.

The belt elastic material 96 comprises a waist elastic material 98 and a side elastic material 100. The waist elastic material 98 may comprise one or more of elastic elements such as strands or panels extending in the transverse direction. The side elastic material 100 also may comprise one or more of elastic elements such as strands or panels extending in the transverse direction. The waist elastic material 98 is continuously disposed along the distal edge 88 of the front and back belt portion 84, 86. The side elastic material 100 is preferably disposed in the side panel 82 of the front and back belt portion 84, 86. In the embodiment shown in FIG. 2, the waist elastic material 98 and the side elastic material 100 comprise a plurality of elastic strands which are disposed at a constant interval in the longitudinal direction. Alternatively, the waist elastic material 98 and the side elastic material 100 may be disposed at a different interval in the longitudinal direction. No elastic material may be provided in a portion of the central panel 80 of the front and back belt portion 84, 86 which overlaps with the absorbent core 62, preferably with the front and back waist panel 52, 54 of the main body 38. Alternatively, no elastic material may be provided in the entirety of the central panel 80. However, an elastic material may be provided in the central panel 80 if it is necessary. The belt elastic material 96 is interposed between the outer layer 92 and the inner layer 94 and joined therebetween in an uncontracted condition of the belt elastic material 96 such that the front and back belt portion 84, 86 provides elasticity when the diaper 20 is used.

Figure 9:
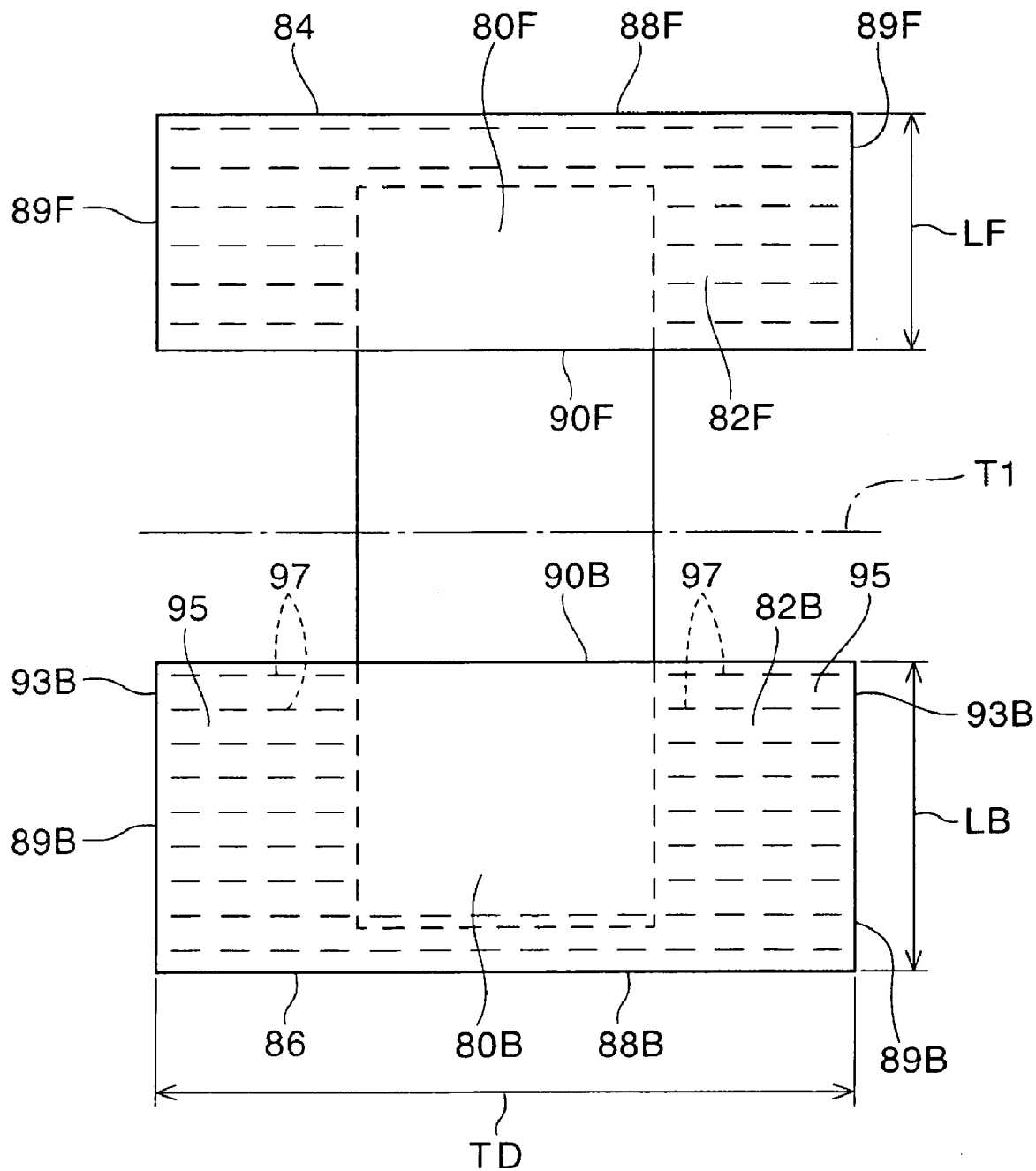
FIG. 9 is a schematic plan view of the garment of the present invention in its flat uncontracted condition showing the outer surface.
Figure 10:
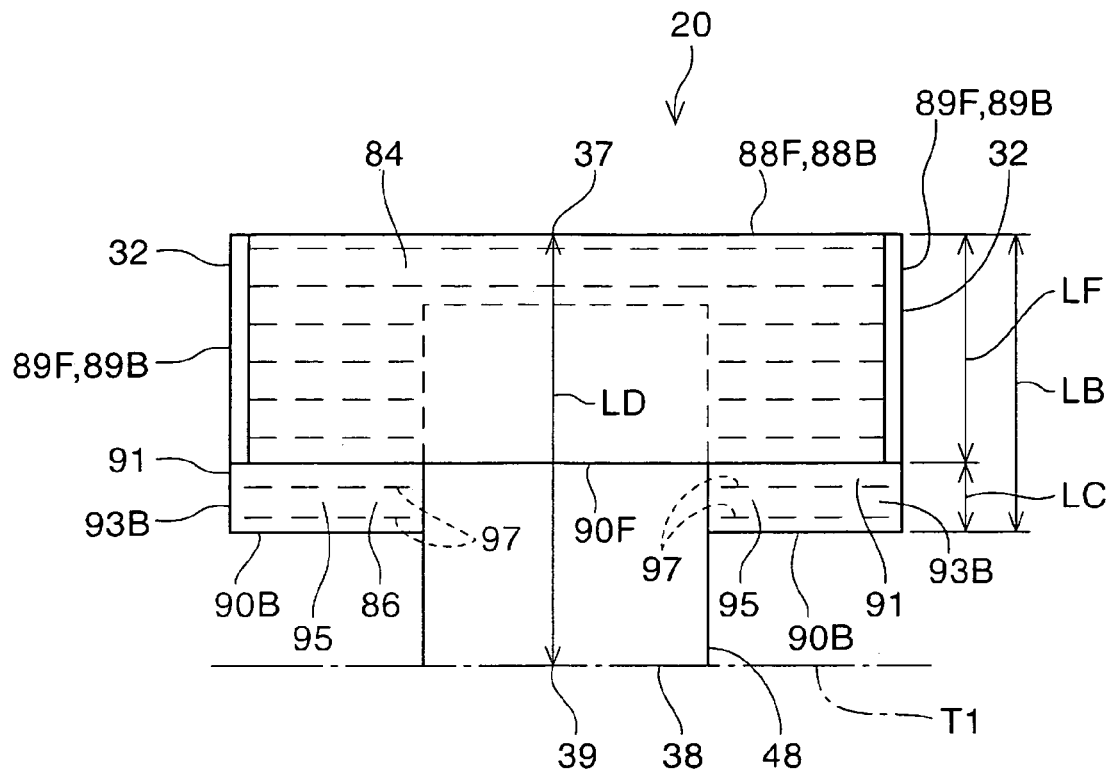
FIG. 10 is a schematic front view of the assembled pull-on garment in its flat uncontracted condition.

The front side panel 82F has a longitudinal length LF defined by the front side edge 89F of the front belt portion 84 and the back side panel 82B has a longitudinal length LB defined by the back side edge 89B of the back belt portion 86 (refer to FIGS. 9 and 10). The front belt portion 84 and the back belt portion 86 are formed such that the longitudinal lengths LB of the back side panels 82B of the back belt portion 86 are greater than the longitudinal lengths LF of the front side panels 82F of the front belt portion 84. The front belt portion 84 and the back belt portion 86 are formed by cutting a belt layer web along a cut line. The forming process will be described in detail hereinbelow. In the embodiment shown in FIGS. 9 and 10, the back central panel 80B also has a greater longitudinal length LB between the back distal edge 88B and the back proximal edge 90B than the longitudinal length LF of the front central panel 80F between the front distal edge 88F and the front proximal edge 90F. Therefore, the back belt portion 86 has a greater longitudinal length LB between the back distal edge 88B and the back proximal edge 90B along its entire width of the back belt portion 86 in the transverse direction than the longitudinal length LF of the front belt portion 84 between the front distal edge 88F and the front proximal edge 88F. When the diaper is assembled to form the waist opening 36 and the leg openings 34, the diaper 20 is folded along the transverse centerline T1 such that the front distal edge 88F is aligned with the back distal edge 88B. The front side edge 89F is also aligned with a portion of the back side edge 89B. Then the front panel portion 84 and the back panel 86 portion are joined at or adjacent the front and back side edges 89F, 89B at the seams 32. The front and back proximal edges 90F, 90B, however, are not aligned to one another as shown in FIG. 10. The back proximal edge 90B is disposed longitudinally closer than the front proximal edge 90F relative to a longitudinally most distant point 39 of the crotch panel 56 from the waist opening edge 37 such that the proximal portion 93B of the back side panel 82B extends toward the crotch panel 56 of the main body 38 beyond the front proximal edge 90F. Thus, the proximal portion 93B of the back side panel 82B provides a buttock cover 95. The side edge of the proximal portion 93B is not joined to anywhere and is free from attachment.

The dimension of the buttock cover 95 should be carefully selected to provide an effective function of buttock cover. The ratio of the longitudinal length LB of the back side edge 89B to the longitudinal length LF of the front side edge 89F is preferably between about 1.1 and about 2.0, more preferably between about 1.1 and about 1.5 in a laid out flat configuration of the garment. The longitudinal length LC shown in FIG. 10 is the difference between LB and LF to provide the buttock cover 95. The ratio of the length LC to the length LF is preferably between about 0.1 and about 1.0, more preferably about 0.1 and about 0.5 in a laid out flat configuration of the garment. The longitudinal garment length LD is the distance from the waist opening edge 37 to a longitudinally most distant point 39 of the crotch panel 56 from the waist opening edge 37 when the garment is laid out flat. The longitudinal length LB of the back side edge 89B is preferably between about 50% and 100%, more preferably about 60% and about 80% of the longitudinal garment length LD when the garment is laid out flat. The garment having these dimension characteristics provides an effective buttock cover without hindering the wearer from inserting legs into the leg opening.

Figure 11:
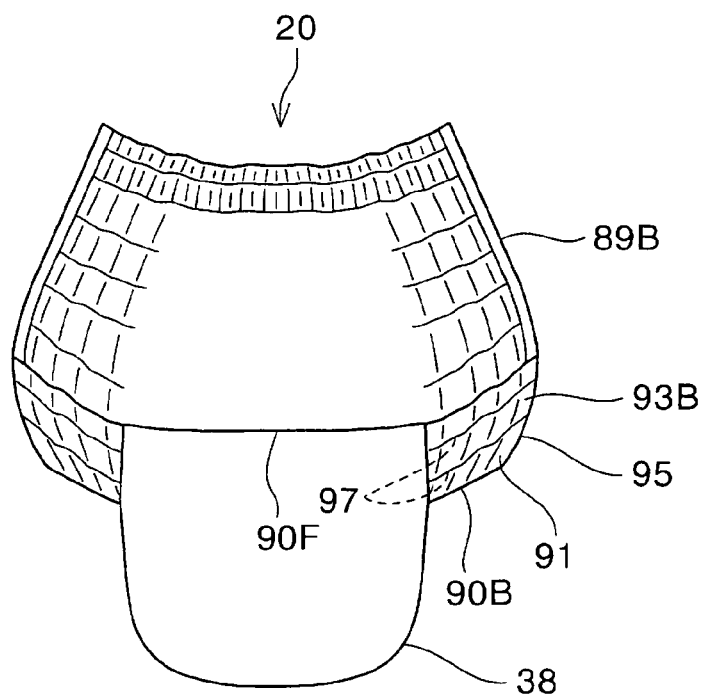
FIG. 11 is a schematic front view of the assembled pull-on garment in its contracted condition.
Figure 12:
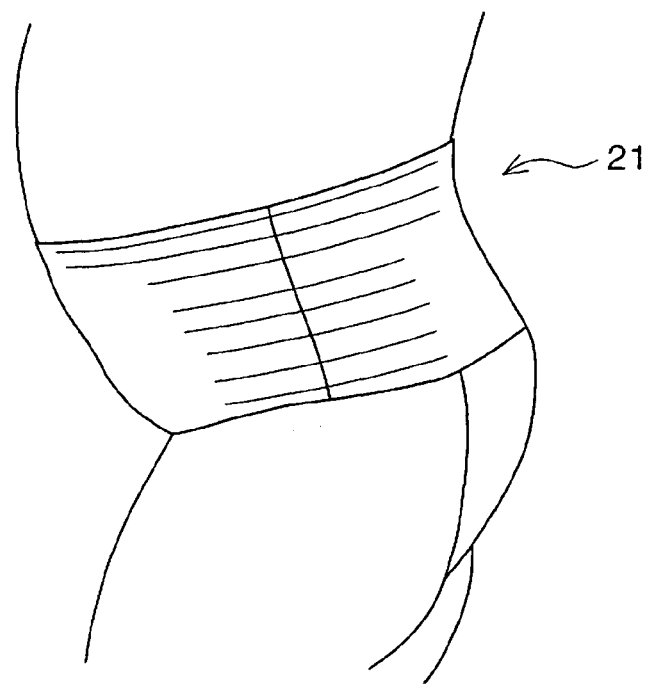
FIG. 12 is a schematic side view of the garment in its use condition for comparison.
Figure 13:
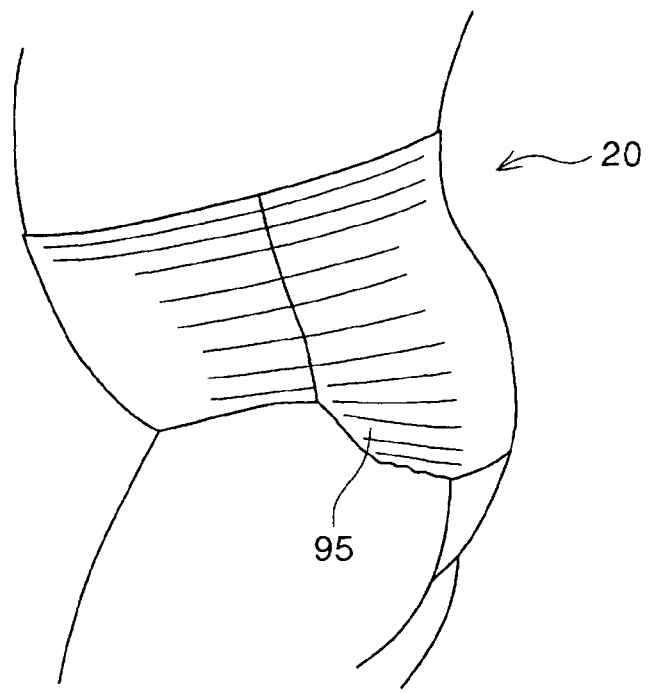
FIG. 13 is a schematic side view of the garment of the present invention in its use condition.

The buttock cover 95 has a buttock cover elastic material 97. The buttock cover elastic material 97 may be formed with the same material as the belt elastic material 96. However, the buttock cover elastic material 97 has greater contraction force than the belt elastic material on the back side panel 82B. The greater contraction force of the buttock cover elastic material 97 helps gathering the belt layer 91 to provide an aesthetic appearance with the buttock cover 95. FIG. 11 shows the diaper 20 in a relaxed condition. As shown, since the buttock cover elastic material 97 gathers the belt layer 91, the proximal portion 93B of the back side panel 82B is pulled to reduce angular appearance of the buttock cover 95. FIGS. 12 and 13 show a diaper worn by a wearer. The diaper 21 shown in FIG. 12 does not have a buttock cover and can not sufficiently cover the buttock of the wearer. However, the diaper 20 of the present invention shown in FIG. 13 has a buttock cover 95 and sufficiently covers the buttock of the wearer.

The patch sheet 44 printed with a graphic 46 is provided on the diaper 20 to provide an aesthetic appearance. The graphic 46 may be any graphic to enhance aesthetic appearance, such as visual characters, educational signs or marks. The patch sheet 44 may comprise any known material such as a plastic film, a woven, a nonwoven or tissues and may have any shape. The patch sheet 44 may also comprise a single sheet or two or more separate sheets. In the embodiment shown in FIG. 1, the patch sheet 44 comprises a single rectangular nonwoven having high breathability. The printing may be made by any known process such as flexographic printing, ink-jet printing, screen printing, or rotogravure printing.

The patch sheet 44 is a material separate from any elements constituting the diaper 20. The patch sheet 44 may be joined anywhere as far as it can be seen by the user of the diaper. The patch sheet 44 is preferably joined somewhere outside the liquid impervious backsheet 60 of the main body 38, preferably outside the outer cover layer 42, more preferably outside the inner layer 94 of the front and back belt portion 84, 86 to reduce hazy appearance of the graphic 46. The patch sheet 44, however, is joined inside the outer layer 94 of the front and back belt portion 84, 86 to prevent an ink rub-off problem caused by abrasion of the ink layer of the graphic 46 with other substrates such as cloths or floors. In the embodiment shown in FIG. 6, the patch sheet 44 with the graphic 46 is disposed and joined between the inner layer 92 and the outer layer 94 of the front and back belt portion 84, 86. However, if the front and back belt portion 84, 86 of the diaper 20 is formed with only the belt elastic material 96 and the outer layer 94 and does not have the inner layer 92, the patch sheet 44 may be disposed between the liquid impervious backsheet 60 of the main body 38 and the outer layer 94 of the front and back belt portion 84, 86. In such a case, the patch sheet 44 may be joined to the liquid impervious backsheet 60, the outer layer 94 or both of them.

The position of the patch sheet 44 is selected such that the patch sheet 44 is disposed between the distal end edge 108 and the proximal end edge 110 of the front and back belt portion 84, 86. The distal end edge 108 and the proximal end edge 110 do not cross any portion of the graphic 46 (refer to FIG. 1). The entirety of the graphic 46 is covered by only the outer layer 92. Therefore, the graphic appearance is the substantially same anywhere in the patch sheet 44 not to make a part of the graphic 46 to have hazier appearance than other parts of the graphic 46.

The patch sheet 44 is preferably disposed in the central panel 80 of the front and back panel portion 84, 86 in which the belt elastic material 96 is not present as shown in FIG. 1. However, the patch sheet 44 may be disposed in the area such as in the side panel 82 in which the belt elastic material 96 is present. The patch sheet 44 may be coextensive with the outer layer 92 of the front and back belt portion 84, 86 such that the patch sheet 44 has the same shape as the outer layer 92. However, it is preferable that the patch sheet 44 is smaller than the outer layer 92 to reduce bulkiness of the front and back belt portion 84, 86. The front and back belt portion 84, 86 may have two or more patch sheets with a graphic which are disposed between the distal end edge 108 and the proximal end edge 110 of the front and back belt portion 84, 86.

Figure 14:
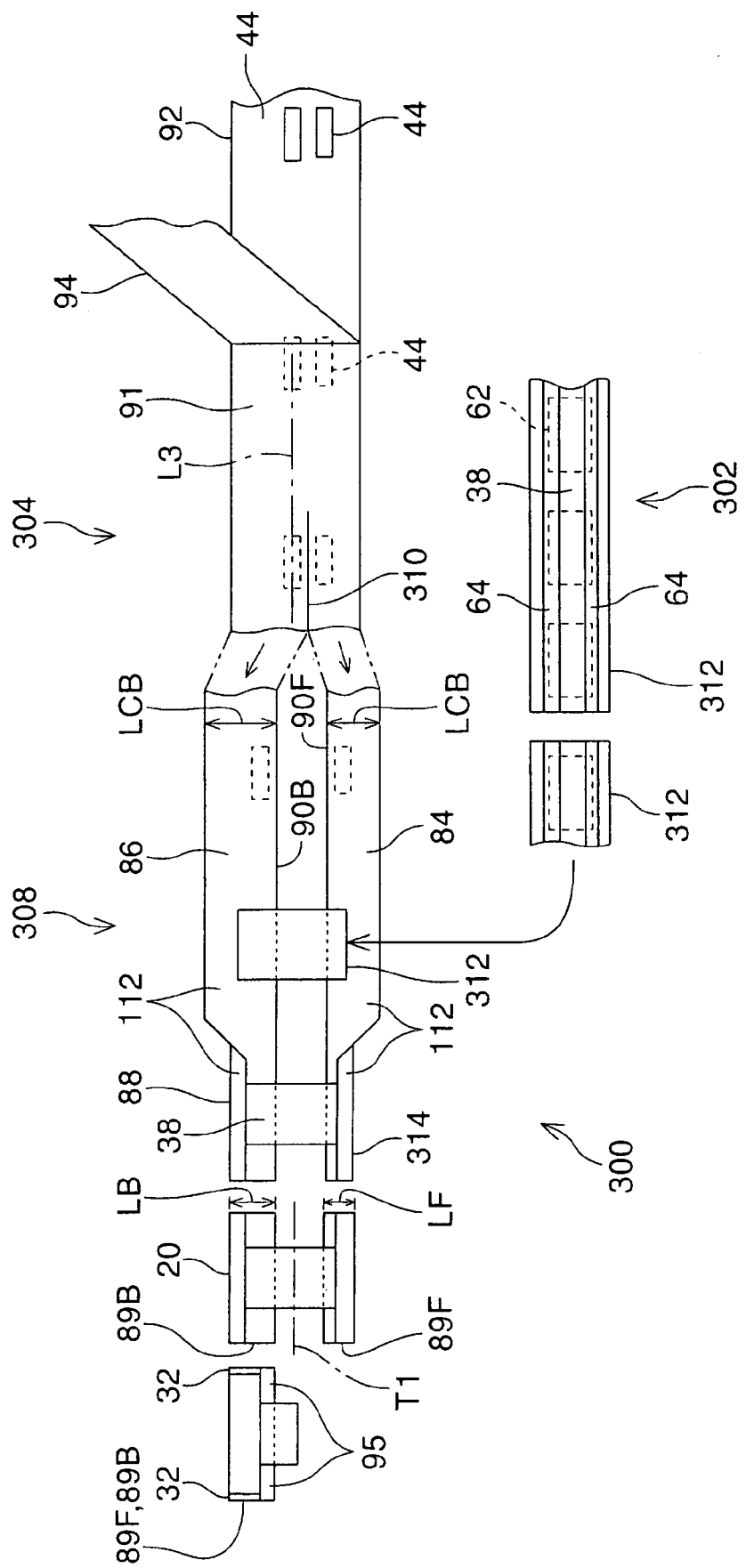
FIG. 14 is a schematic view showing the process for forming the pull-on garment shown in FIG. 1.

The front belt portion 84 and the back belt portion 86 are formed by cutting the belt layer web along a cut line. FIG. 14 shows a schematic view to explain the process for forming the diaper 20. The process 300 shown in FIG. 14 primarily comprises three sections; a main body forming section 302, a belt forming section 304 and an assembly section 308. Since FIG. 14 is a schematic view, it should be noted that various parts of the diaper have been omitted, such as the belt elastic material and the leg elastic material.

The main body forming process 302 combines elements forming the main body 38 such as the topsheet 58, the backsheet 60, the absorbent core 62 and the barrier leg cuff 64 such that the absorbent core 62 is sandwiched between the topsheet 58 and the absorbent core 62. The outer cover layer 42 (not shown in FIG. 14) is joined to the backsheet 60 (not shown in FIG. 14) and the leg elastic material 118 (not shown in FIG. 14) is sandwiched between the backsheet 60 and the outer cover layer 42. These elements are joined to each other by any known means such as adhesives or heat bonding to form an intermediate assembly 312. The intermediate assembly 312 then cut into the individual intermediate assembly 312. The individual intermediate assembly 312 is turned by 90 degree and fed into the assembly section 308.

The belt forming section 304 combines the outer layer web 92 and the inner layer web 94 to form a continuous belt layer web 91. When joining the outer layer web 92 and the inner layer web 94, the patch sheet 44 is sandwiched therebetween. The continuous belt layer web 91 is cut along a straight cut line 310 which corresponds to the proximal edge 90F, 90B to form a continuous front belt web 84 and a continuous back belt web 86. The cut line 310 is biased from the longitudinal centerline L3 of the continuous belt layer web 91 to differentiate the length LCF of the continuous front belt web 84 and the length LCB of the continuous back belt web 86 in the cross machine direction. The cross machine direction means the direction crossing the machine direction at a right angle. The machine direction means the direction where the component material is conveyed in the manufacturing process, which is in parallel to the longitudinal centerline L3. The belt elastic material 96 and the buttock cover elastic material 97 (not shown in FIG. 14) are also joined between the inner layer web 94 and the outer layer web 92. Then the continuous front belt web 84 and the continuous back belt web 86 are separated from one another.

The assembly section 308 combines the individual intermediate assembly 312 with the continuous front belt web 84 and the continuous back belt web 86. The individual intermediate assembly 312 is placed on the continuous front and back belt webs 84, 86 at a predetermined interval to provide the side panel between each of the individual intermediate assemblies 312. The end flap 112 of the front and back belt webs 84, 86 is folded inwardly along the distal edge 88 to form a continuous diaper assembly 314 comprising the main body 38, the outer cover layer 42 (not shown in FIG. 14) and the front and back belt webs 84, 86. The continuous diaper assembly 314 thus formed is cut into each individual diaper 20. The individual diaper 20 has the longitudinal length LB of the back side edge 89B being greater than the longitudinal length LF of the front side edge 89F. The individual diaper 20 is then folded along the transverse centerline T1 in the crotch region and the front and back belt 84, 86 is joined at the seam 32 adjacent the side edges 89F, 89B to form the waist opening and the leg openings. The buttock cover 95 is also formed as shown in FIG. 14 without requiring trimming any portion of the belt layer web.

Figure 15:
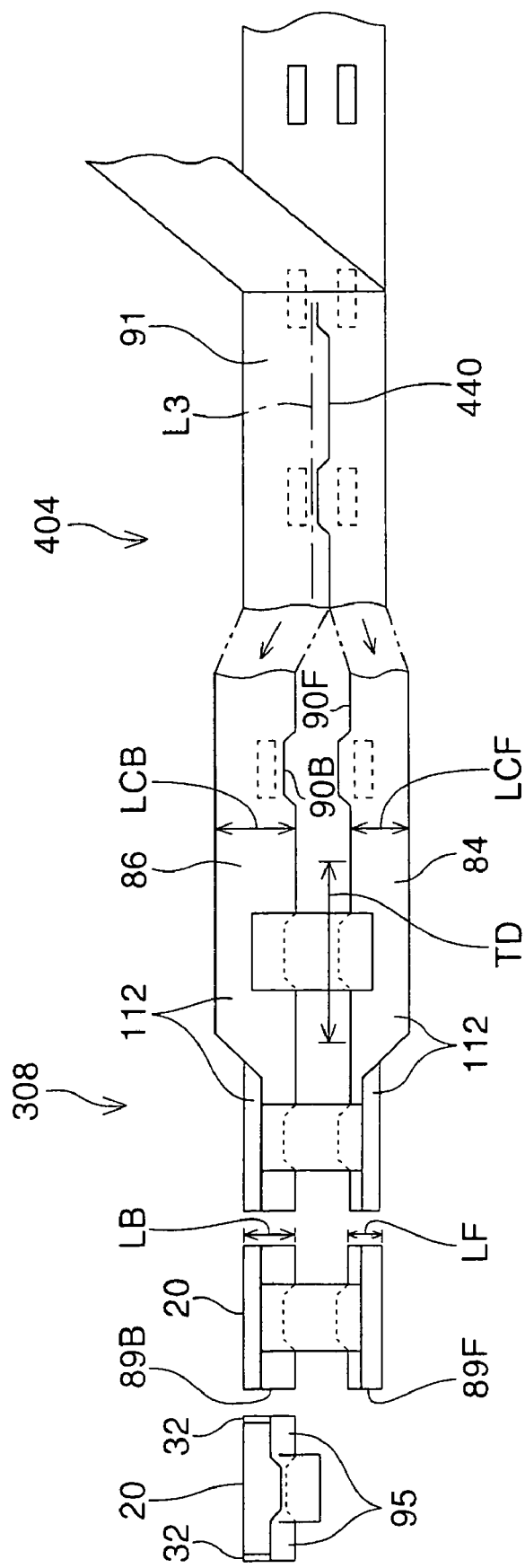
FIG. 15 is a schematic view of an alternative embodiment for the process for forming the pull-on garment.

FIG. 15 shows an alternative embodiment of the belt forming section. In the belt forming section 404 in FIG. 15, the continuous belt layer web 91 is cut along a wavy cut line 410 which corresponds to the proximal edge 90F, 90B to form a continuous front belt web 84 and a continuous back belt web 86. The wavy cut line may comprise a combination of straight lines, a combination of curved lines or a combination of straight lines and curved lines. The regular wavy cut line comprises a plurality of repeating unit, each of which has a repeating length corresponding to the transverse width TD of the diaper 20 (see FIGS. 9 and 15). In the embodiment shown in FIG. 15, the wavy cut line 410 comprises a combination of straight lines such that the wavy cut line 410 has a plurality of trapezoidal portions protruding alternately oppositely. Such a wavy cut line 410 differentiates the length LCF of a portion corresponding to the front side panel 82F and the length LCB of a portion corresponding to the back side panel 82B in the cross machine direction. The continuous front belt web 84 and the continuous back belt web 86 thus formed are forwarded to the assembly section 308 to form an individual diaper 20. The individual diaper 20 has the longitudinal length LB of the back side edge 89B being greater than the longitudinal edge LF of the front side edge 89F. The buttock cover 95 is also formed as shown in FIG. 15.

Figure 16:
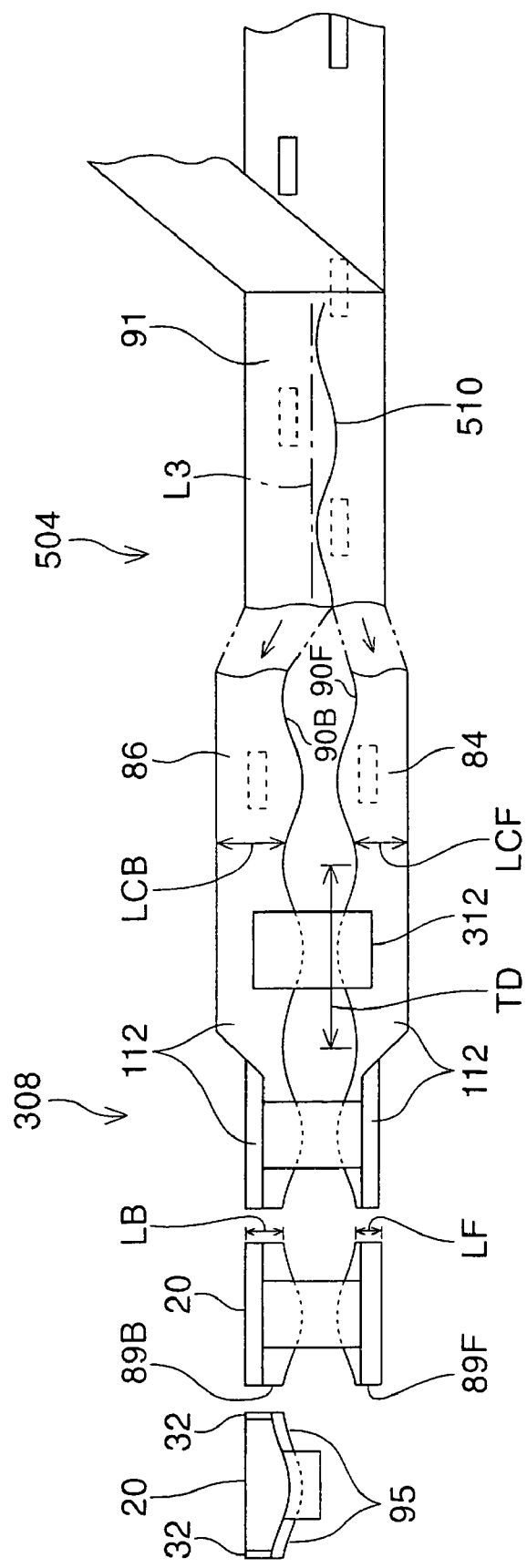
FIG. 16 is a schematic view of an alternative embodiment for the process for forming the pull-on garment.

FIG. 16 shows an alternative embodiment of the belt forming section. In the belt forming section 504 in FIG. 16, the continuous belt layer web 91 is cut along a wavy cut line 510 which corresponds to the proximal edge 90F, 90B to form a continuous front belt web 84 and a continuous back belt web 86. In the embodiment shown in FIG. 16, the wavy cut line 510 comprises a combination of curved lines, more concretely a sinusoidal line. The wavy cut line 510 has a repeating unit, each of which has a repeating length corresponding to the transverse width TD of the diaper 20. After the continuous belt layer web 91 is cut into the continuous front belt web 84 and the continuous back belt web 86, the continuous front and back belt webs 84 and 86 are phased such that the length LCB of a portion corresponding to the back side panel 86 is greater than the length LCF of a portion corresponding to the front side panel 82F. The continuous front belt web 84 and the continuous back belt web 86 thus formed are forwarded to the assembly section 308 to form an individual diaper 20. The individual diaper 20 has the longitudinal length LB of the back side edge 89B being greater than the longitudinal length LF of the front side edge 89F. The buttock cover 95 is also formed as shown in FIG. 15.

Figure 17:
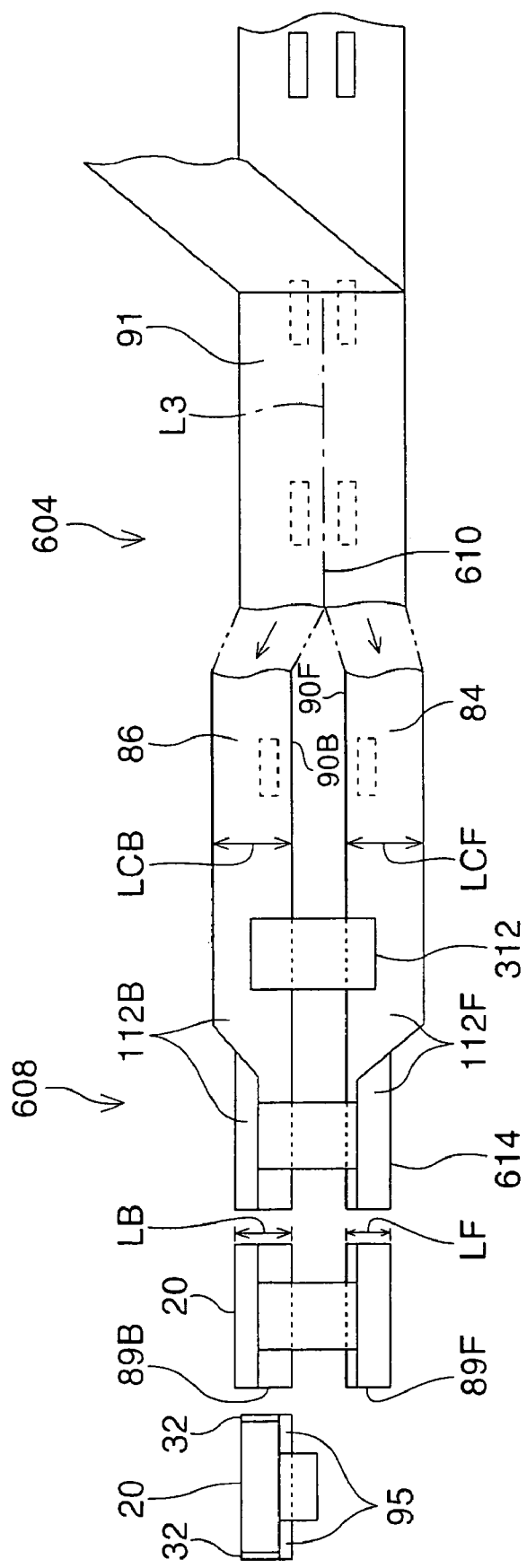
FIG. 17 is a schematic view of an alternative embodiment for the process for forming the pull-on garment.

FIG. 17 shows an alternative embodiment of the belt forming section and the assembly section. In the belt forming section 604 in FIG. 17, the continuous belt layer web 91 is cut along a straight cur line 610 which corresponds to the proximal edge 90F, 90B to form a continuous front belt web 84 and a continuous back belt web 86. The straight cut line 610 corresponds to the longitudinal centerline L3 of the continuous belt layer web 91. Therefore, the length LCF of the continuous front belt web 84 and the length LCB of the continuous back belt web 86 are the same in the cross machine direction in the embodiment shown in FIG. 17. In the assembly section 608, the end flap 112F, 112B of the front and back belt webs 84, 86 is folded inwardly along the transverse waist edge 88 to form a continuous diaper assembly 614. While the length LCF and the length LCB are the same, the length of the end flap in the cross machine direction which is folded over is different between the front belt portion 84 and the back belt portion 86. The length of the back end flap 112B has the folded length being greater than the length of the front end flap 112F whereby the individual diaper 20 is formed to have the longitudinal length LB of the back side edge 89B being greater than the longitudinal length LF of the front side edge 89F. The individual diaper 20 is then folded along the transverse centerline T1 in the crotch region and the front and back belt portion 84, 86 is joined at the seam 32 adjacent the side edges 89F, 89B to form the waist opening and the leg openings. The buttock cover 95 is also formed as shown in FIG. 17.

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A disposable pull-on garment having a waist opening and two leg openings and extending in a longitudinal direction and a transverse direction, the pull-on garment comprising a transverse centerline an absorbent main body and a ring-like elastic belt, wherein:

the absorbent main body comprises a liquid pervious topsheet, a liquid impervious backsheet, and an absorbent core disposed therebetween, the absorbent main body has left and right longitudinally extending side edges, front and back transversely extending end edges, longitudinally opposing front and back waist panels, and a crotch panel between the waist panels;

the ring-like elastic belt comprises a front belt portion and a back belt portion, each belt portion comprising:

a belt layer;

a belt elastic material joined to the belt layer;

a proximal edge that is parallel to the transverse centerline;

a distal edge that is parallel to the transverse centerline;

the proximal edge being located closer than the distal edge relative to the crotch panel of the absorbent main body;

longitudinally extending left and right side edges connecting the proximal and distal edges;

a central panel; and left and right side panels contiguous with the central panel, each side panel having a longitudinal length defined by the respective side edge of the respective belt portion;

the central panel of the front belt portion is joined to the front waist panel of the absorbent main body, the central panel of the back belt portion is joined to the back waist panel of the absorbent main body, and the respective left and right side panels of the front belt portion and the back belt portion are each joined together to form a seam at or adjacent to the respective left and right side edges to form the waist opening and the two leg openings; and the longitudinal lengths of each the side panels of the back belt portion are greater than the longitudinal lengths of each of the respective side panels of the front belt portion at the seams; and wherein the waist opening has a waist opening edge and the longitudinal length of the side edge of each of the side panels of the back belt portion is between about 50% and 100% of a distance from the waist opening edge to a longitudinally most distant point of the crotch panel from the waist opening edge when the garment is laid out flat.

2. The disposable pull-on garment of claim 1 wherein the proximal edge and the distal edge are substantially parallel.

3. The disposable pull-on garment of claim 1 wherein the proximal edge of each of the side panels of the back belt portion is disposed longitudinally closer than the proximal edge of the each of the side panels of the front belt portion relative to a longitudinally most distant point of the crotch panel from the waist opening edge.

4. The disposable pull-on garment of claim 1 wherein the ratio of the longitudinal length of the side edge of each of the side panels of the back belt portion to the longitudinal length of the side edge of the respective side panel of the front belt portion is between about 1.1 and about 2.0 in a laid out flat condition of the garment.

5. The disposable pull-on garment of claim 2 wherein the proximal edges of the front belt portion and the back belt portion are straight.

6. The disposable pull-on garment of claim 1 wherein the longitudinal length of the side edge of each of the side panels of the back belt portion is between about 60% and about 80% of the distance from the waist opening edge to the longitudinally most distant point of the crotch panel from the waist opening edge when the garment is laid out flat.

* * * * *